United States Patent [19]
Klein

[11] Patent Number: 4,793,332
[45] Date of Patent: Dec. 27, 1988

[54] HANDLE FOR A MOUTH WASH DEVICE

[75] Inventor: Horst Klein, Kelkheim-Fischbach, Fed. Rep. of Germany

[73] Assignee: Blendax-Werke R. Schnieder, Fed. Rep. of Germany

[21] Appl. No.: 160,777

[22] Filed: Feb. 26, 1988

Related U.S. Application Data

[63] Continuation of Ser. No. 320,557, Nov. 12, 1981, abandoned.

[30] Foreign Application Priority Data

Nov. 22, 1980 [DE] Fed. Rep. of Germany ....... 3044025

[51] Int. Cl.⁴ ............................................. A61H 9/00
[52] U.S. Cl. ...................................................... 128/66
[58] Field of Search ................................ 128/66, 62 A

[56] References Cited

U.S. PATENT DOCUMENTS 3,593,707 7/1971 Pifer ....................................... 128/66

Primary Examiner—Robert Peshock
Attorney, Agent, or Firm—Connolly and Hutz

[57] ABSTRACT

A handle for a mouth was device includes a switch for selectively connecting the liquid intake with a canal having bristleless a single-jet spray or with a canal having a bristleless multi-jet spray.

4 Claims, 1 Drawing Sheet

HANDLE FOR A MOUTH WASH DEVICE

CROSS-REFERENCE TO RELATED APPLICATION

This is a continuation of application Ser. No. 320,557 filed Nov. 12, 1981 (now abandoned).

BACKGROUND OF INVENTION

The invention concerns a handle with a spray nozzle, pertaining to a mouth wash device. The handle is capable of producing either one spray jet only or a number of spray jets.

Mouth wash device handles with spray nozzles have long been known in various forms, for instance from German Auslegeschriften (DE-AS) Nos. 20 50 687, 22 00 083 and 23 46 677 as well as German Offenlegungsschriften Nos. 14 66 963 and 27 46 453. In each case, these nozzles are capable of producing either one single spray jet or a number of spray jets. Both types of forms have advantages as well as disadvantages.

It is, for instance, advantageous to use a single jet nozzle when the purpose is a thorough cleaning of the interdental spaces. The use of such a nozzle as described, e.g., in U.S. Pat. No. 3,227,158 is, however, not of advantage if at the same time the gums are to be massaged since the resulting pressure on the gums is too localized and strong and consequently may cause experience of pain or, in some cases, even bleeding of the gums. Thus, the use of a multi-jet water flow is advantageous, which, however, results in less thorough cleaning of the interdental spaces than a single jet water flow.

SUMMARY OF INVENTION

An object of the invention is to create the possibility of developing a universally applicable spray nozzle for mouth wash devices such as "mouth showers", which allows both cleaning of the spaces between the teeth and optimum massage of the gums.

In accordance with the invention utilization is made of a handle, which has a relatively simple construction, and which is consequently also possible to manufacture inexpensively.

More specifically the handle of the spray nozzle of the mouth wash device is provided with a nozzle tube having a nozzle head that can produce both one single spray jet and also a number of jets.

In the preferred practice of the invention the handle, ; provided in a known manner with a liquid feed line, has two canals for the liquid, arranged in a longitudinally movable inset, whereby one or the other of the canals can be connected with the liquid intake by means of a slide switch. In this manner, the nozzle tube can be attached to the handle, has two different spray nozzles at its upper end and also two parallel canals for liquid, connected with the canals in the handle, whereby one canal ends in a single jet nozzle and the other canal in a multi-jet spray nozzle.

When the mouth shower is being used, the liquid intake can be controlled by moving the canal inset by means of the switch in such a manner that the water will exit in either one jet through the single jet nozzle or in several jets through the other nozzle. In this manner, it is possible to produce an easily adjusted, simply constructed mouth shower that will satisfy all requirements of dental medicine. The design of the mouth shower with respect to motor, pump, water container, etc., is already known and does not constitute an object of the invention.

In principle, the same applies for the individual design of the single jet and/or multiple jet nozzles. So, for instance, the single jet nozzle can be designed in accordance with the description in the above-mentioned U.S. Pat. No. 3,227,158.

Suitable multiple nozzles are described, for instance, in the documents DE-AS Nos. 20 50 687 and 22 00 083, which are also referred to in the foregoing. The details of these patents are incorporated herein by reference thereto.

A particularly advantageous embodiment of the multiple nozzles may be designed so that it contains a movable, slightly conical insert, which fits into the nozzle opening and has a recess in the shape of a truncated cone at the end facing the inside of the nozzle, corresponding to a conical projection of the inside wall of the nozzle. The liquid impulses or the frequency of the impulses can be adjusted in a manner that is also previously known.

THE DRAWINGS

FIG. 1 shows a cross section of a handle for mouth shower, developed in accordance with the invention; and FIG. 2 shows a front view of the handle of FIG. 1 with the attached nozzle.

DETAILED DESCRIPTION

Figure 1:
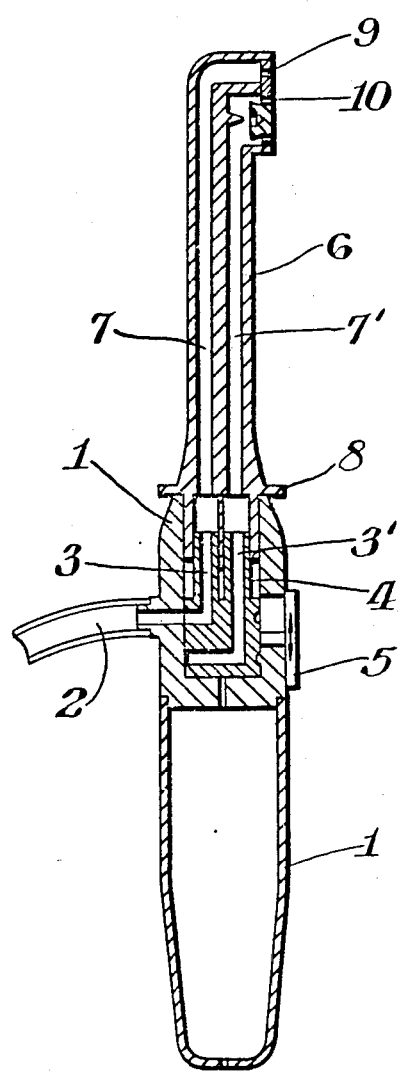
Figure 2:
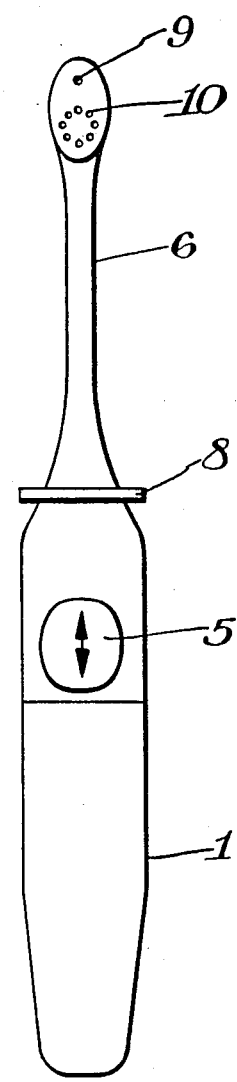

A handle 1 which is provided in a known manner with a liquid intake 2 contains two parallel canals 3, 3' for the liquid which are located in a longitudinally adjustable insert 4, whereby either one of the canals for the liquid 3, 3' can be connected with the liquid intake 2 by means of moving the insert 4. Switch structure 5 is connected to the insert 4 for longitudinally shifting the insert to connect either of the canals 3,3' with the liquid intake 2. The switch structure moves the insert 4 between a first position where one of the canals 3 communicates with the liquid intake 2 and a second position where the other canal 3' communicates with the liquid intake 2. The insert 4 has an intermediate position between its first and second positions for blocking the liquid intake 2. On the handle 1, a nozzle tube 6 is attached, which also has two parallel canals 7, 7' which are to be regarded as continuations of the canals 3 and 3'. Preferably the nozzle tube 6 is attached to the handle 1 in such a manner that it can r be turned, e.g., by means of a knurled screw 8. The canal 3 or 7 leads to the bristleless single jet nozzle 9 located at the head of the nozzle tube 6; canal 3' or 7' leads to the multiple jet nozzle 10.

What is claimed is:

1. In a handle for a mouth wash device, provided with a liquid intake and a spray nozzle attachable to the handle by means of a nozzle tube, the improvement being said handle being provided with a first set of two parallel canals for liquid, said first set of canals being arranged within a longitudinally adjustable insert for selective flow communication with said liquid intake, switch means for controlling said selective flow communication, a nozzle tube attached to said handle, a second set of two parallel canals in said nozzle tube communicating with said first set of canals to form a pair of elongated canals, one of said elongated canals leading to a bristleless single-jet spray nozzle, and the other of said elongated canals leading to a bristleless multi-jet spray nozzle wherein the multijets are generally arranged in a circle.

2. The handle of claim 1 wherein both of said bristleless spray nozzles are mounted to one end of said nozzle tube.

3. The handle of claim 1 wherein the longitudinally adjustable insert is movable by said switch means between a first position where one of the canals of said first set communicates with said liquid intake and a second position where the other canal of said first set communicates with said liquid intake, and the adjustable insert having an intermediate position between the first and second positions for blocking said liquid intake.

4. The handle of claim 1 wherein the liquid intake and the second set of two parallel canals in said nozzle tube are at right angles to one another.

* * * * *